US00PP20542P2

(12) United States Plant Patent
Misato

(10) Patent No.: US PP20,542 P2
(45) Date of Patent: Dec. 8, 2009

(54) ***MANDEVILLA* PLANT NAMED 'SUNPARARENGA'**

(50) Latin Name: *Mandevilla hybrida*
Varietal Denomination: Sunpararenga

(75) Inventor: Tomoya Misato, Yamanashi (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/228,269

(22) Filed: Aug. 11, 2008

(51) Int. Cl.
*A01H 5/00* (2006.01)

(52) U.S. Cl. ..... Plt./232
(58) Field of Classification Search ..... Plt./232

See application file for complete search history.

*Primary Examiner*—June Hwu
(74) *Attorney, Agent, or Firm*—C. A. Whealy

(57) ABSTRACT

A new and distinct cultivar of *Mandevilla* plant named 'Sunpararenga', characterized by its upright and vining plant habit; relatively small glossy foliage; freely branching habit; freely flowering habit; deep red-colored flowers; and long flowering period.

1 Drawing Sheet

Botanical designation: *Mandevilla hybrida.*
Cultivar denomination: 'Sunpararenga'.

BACKGROUND OF THE INVENTION

The present invention relates to a new and distinct cultivar of *Mandevilla*, botanically known as *Mandevilla hybrida* and hereinafter referred to by the name 'Sunpararenga'.

The new *Mandevilla* plant is a product of a planned breeding program conducted by the Inventor in Higashiomi, Shiga, Japan. The objective of the breeding program is to create new compact, vining and freely-branching *Mandevilla* cultivars with numerous attractive flowers.

The new *Mandevilla* originated from a cross-pollination made by the Inventor in Higashiomi, Shiga, Japan in February, 2002, of a proprietary selection of *Mandevilla hybrida* identified as code number M35-4, not patented, as the female, or seed parent with a proprietary selection of *Mandevilla hybrida* identified as code number M28-3, not patented, as the male, or pollen, parent. The new *Mandevilla* was discovered and selected by the Inventor as a single flowering plant from within the progeny of the stated cross-pollination in a controlled greenhouse environment in Higashiomi, Shiga, Japan in November, 2003.

Asexual reproduction of the new *Mandevilla* plant by cuttings in Higashiomi, Shiga, Japan, since December, 2003, has shown that the unique features of this new *Mandevilla* plant are stable and reproduced true to type in successive generations.

SUMMARY OF THE INVENTION

Plants of the new *Mandevilla* have not been observed under all possible environmental conditions. The phenotype may vary somewhat with variations in environment such as temperature and light intensity without, however, any variance in genotype.

The following traits have been repeatedly observed and are determined to be the unique characteristics of 'Sunpararenga'. These characteristics in combination distinguish 'Sunpararenga' as a new and distinct cultivar:

1. Upright and vining plant habit.
2. Relatively small glossy foliage.
3. Freely branching habit.
4. Freely flowering habit.
5. Deep red-colored flowers.
6. Long flowering period.

Plants of the new *Mandevilla* can be compared to plants of the female parent selection. Plants of the new *Mandevilla* differ from plants of the female parent selection in the following characteristics:

1. Leaves of plants of the new *Mandevilla* are elliptic in shape whereas leaves of plants of the female parent selection are ovate in shape.
2. Plants of the new *Mandevilla* and the female parent selection differ in flower color as plants of the female parent selection have lighter red-colored flowers.

Plants of the new *Mandevilla* can be compared to plants of the male parent selection. Plants of the new *Mandevilla* differ from plants of the male parent selection in the following characteristics:

1. Plants of the new *Mandevilla* have thicker stems than plants of the male parent selection.
2. Plants of the new *Mandevilla* and the male parent selection differ in flower color as plants of the male parent selection have light pink-colored flowers.

Plants of the new *Mandevilla* can be compared to plants of the *Mandevilla* 'Sunmanderemi', disclosed in a U.S. Plant Pat. No. 16,449. Plants of the new *Mandevilla* differ from plants of 'Sunmanderemi' in the following characteristics:

1. Plants of the new *Mandevilla* have thicker stems than plants of 'Sunmanderemi'.
2. Plants of the new *Mandevilla* have shorter internodes than plants of 'Sunmanderemi'.
3. Plants of the new *Mandevilla* have larger leaves than plants of 'Sunmanderemi'.
4. Plants of the new *Mandevilla* have smaller flowers than plants of 'Sunmanderemi'.
5. Plants of the new *Mandevilla* and 'Sunmanderemi' differ in flower color as plants of 'Sunmanderemi' have lighter red-colored flowers.

BRIEF DESCRIPTION OF THE PHOTOGRAPHS

The accompanying colored photographs illustrate the overall appearance of the new *Mandevilla* plant, showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunpararenga' grown in a container.

The photograph at the bottom of the sheet is a close-up view of typical flowers and flower buds of 'Sunpararenga'.

DETAILED BOTANICAL DESCRIPTION

The aforementioned photographs and following observations, measurements and values describe plants grown in Higashiomi, Shiga, Japan, under commercial practice during the late spring and early summer in an outdoor nursery. During the production of the plants, day temperatures averaged 25° C. and night temperatures averaged 15° C. Plants had been growing for five and six months when the description and photographs, respectively, were taken. In the following description, color references are made to The Royal Horticultural Society Colour Chart, 2001 Edition, except where general terms of ordinary dictionary significance are used.

Botanical classification: *Mandevilla hybrida* 'Sunpararenga'.

Parentage:

*Female, or seed, parent.*—Proprietary selection of *Mandevilla hybrida* identified as code number M35-4, not patented.

*Male, or pollen, parent.*—Proprietary selection of *Mandevilla hybrida* identified as code number M28-3, not patented.

Propagation:

*Type.*—By vegetative cuttings.

*Time to initiate roots.*—About two weeks at 23° C. to 25° C.

*Time to produce a rooted young plant.*—About five to six weeks at 23° C. to 25° C.

*Root description.*—Fibrous; light brown in color.

*Rooting habit.*—Freely branching; moderately dense.

Plant description:

*Form.*—Upright and vining plant habit. Vigorous growth habit.

*Plant height.*—About 42 cm.

*Lateral branch description.*—Length: About 128.6 cm. Diameter: About 2.8 mm. Internode length: About 6.4 cm. Strength: Strong. Texture: Smooth, glabrous. Color, young: Close to 146B overlain with close to 177A. Color, mature: Close to 187A.

Foliage description:

*Arrangement.*—Opposite, simple.

*Length.*—About 7.1 cm.

*Width.*—About 4.1 cm.

*Shape.*—Elliptic.

*Apex.*—Cuspidate.

*Base.*—Obtuse.

*Margin.*—Entire.

*Texture, upper and lower surfaces.*—Smooth, glabrous.

*Luster, upper and lower surfaces.*—Glossy.

*Venation pattern.*—Pinnate, reticulate.

*Color.*—Developing leaves, upper surface: Close to 146A. Developing leaves, lower surface: Close to 146C. Fully expanded leaves, upper surface: Close to 139A; venation, close to 145B. Fully expanded leaves, lower surface: Close to 146C; venation, close to 145B.

*Petiole length.*—About 2.1 cm.

*Petiole diameter.*—About 1.1 mm.

Petiole texture, upper and lower surfaces.—Smooth, glabrous.

Petiole color, upper and lower surfaces.—Close to 177A.

Flower description:

Flower type and habit.—Single salverform flowers; flowers racemose; flowers face mostly outwardly. Freely flowering habit, about five flowers per inflorescence.

*Natural flowering season.*—Long flowering period; plants flower from early summer to late autumn in Japan; flowering continuous during this period. Plants initiate flower development about six weeks after planting.

*Flower longevity on the plant.*—About seven to ten days. Flowers not persistent.

*Fragrance.*—Faint, pleasant.

*Inflorescence length.*—About 14 cm.

*Inflorescence diameter.*—About 10 cm.

*Flowers.*—Appearance: Flared trumpet, corolla fused, five-parted; petals imbricate; flowers roughly star-shaped. Diameter: About 7.1 cm. Depth (length): About 6.5 cm. Throat diameter: About 1.6 cm. Tube length: About 5.2 cm. Tube diameter, mid-section: About 1 cm. Tube diameter, base: About 3.5 mm.

*Flower buds.*—Height: About 6.3 cm. Diameter: About 1.1 cm. Shape: Lenticular. Color: Close to 187C.

*Corolla.*—Arrangement/appearance: Single whorl of five petals, fused into flared trumpet; petals imbricate. Petal length: About 2.9 cm. Petal width: About 2.6 cm. Petal shape: Spatulate. Petal apex: Acuminate. Petal margin: Entire; curled outwardly; slightly undulate. Petal texture, upper and lower surfaces: Smooth, glabrous; velvety. Color: Petal, when opening and fully opened, upper surface: Close to 187B. Petal, when opening and fully opened, lower surface: Close to 187C. Tube: Close to 187D. Throat: Close to 31A.

*Sepals.*—Arrangement/appearance: Five per flower in a single whorl. Length: About 9.9 mm. Width: About 2.6 mm. Shape: Lanceolate. Apex: Acute. Base: Truncate. Margin: Entire. Texture, upper and lower surfaces: Smooth, glabrous. Color, immature, upper and lower surfaces: Close to 178B. Color, mature, upper and lower surfaces: Close to 178B.

*Peduncles.*—Length: About 4.9 cm. Diameter: About 1.5 mm. Texture: Smooth, glabrous. Strength: Flexible, but strong. Color: Close to 176B.

*Pedicels.*—Length: About 1.4 cm. Diameter: About 1.9 mm. Texture: Smooth, glabrous. Strength: Flexible, but strong. Color: Close to 174A.

*Reproductive organs.*—Stamens: Quantity/arrangement: Typically five; filaments fused to corolla; anthers, connivent. Anther shape: Ellipsoidal. Anther size: About 1 cm by 1.7 mm. Anther color: Close to 16D. Pollen amount: Scarce. Pollen color: Close to 2C. Pistils: Quantity: Typically one. Pistil length: About 2.7 cm. Stigma shape: Conical. Stigma color:

Close to 150C. Style length: About 2.3 cm. Style color: Close to 150D. Ovary color: Close to 144C.

*Seed/fruit.*—Seed and fruit production has not been observed.

Disease/pest resistance: Plants of the new *Mandevilla* have not been noted to be resistant to pathogens and pests common to *Mandevilla*.

Temperature tolerance: Plants of the new *Mandevilla* have been observed to tolerate temperatures from about 4° C. to about 30° C.

It is claimed:

1. A new and distinct *Mandevilla* plant named 'Sunpararenga' as illustrated and described.

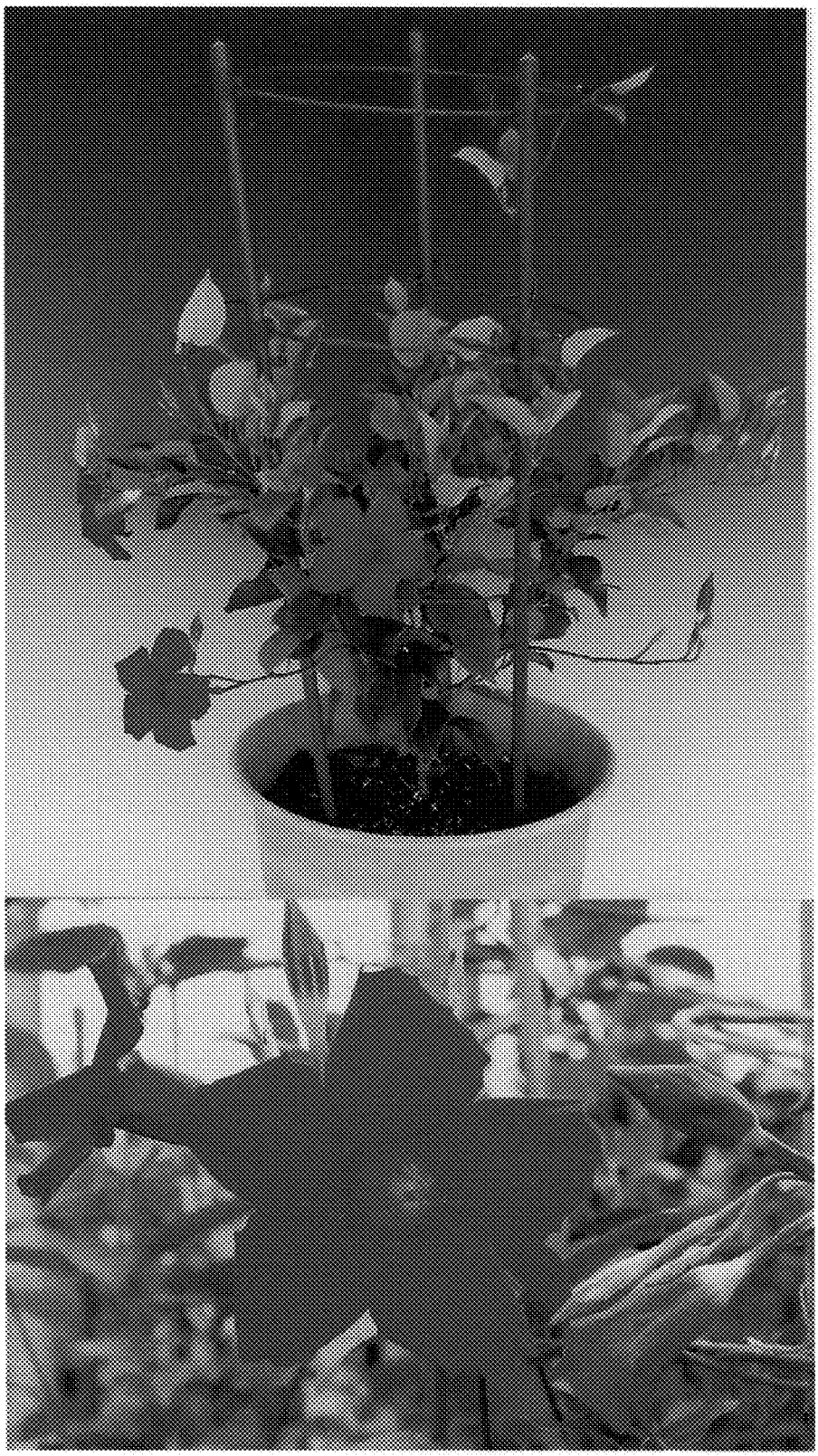

* * * * *